United States Patent
Tass et al.

(10) Patent No.: US 10,786,675 B2
(45) Date of Patent: Sep. 29, 2020

(54) DEVICE AND METHOD FOR EFFECTIVE INVASIVE TWO-STAGE NEUROSTIMULATION

(71) Applicant: Forschungszentrum Juelich GmbH, Juelich (DE)

(72) Inventors: Peter Alexander Tass, Tegernsee (DE); Magteld Zeitler, Malden (NL)

(73) Assignee: FORSCHUNGSZENTRUM JUELICH GMBH, Juelich (DE)

( * ) Notice: Subject to any disclaimer, the term of this patent is extended or adjusted under 35 U.S.C. 154(b) by 240 days.

(21) Appl. No.: 15/738,624

(22) PCT Filed: Jun. 22, 2016

(86) PCT No.: PCT/EP2016/064471
§ 371 (c)(1),
(2) Date: Dec. 21, 2017

(87) PCT Pub. No.: WO2016/207246
PCT Pub. Date: Dec. 29, 2016

(65) Prior Publication Data
US 2018/0178014 A1 Jun. 28, 2018

(30) Foreign Application Priority Data
Jun. 22, 2015 (DE) .................. 10 2015 109 988

(51) Int. Cl.
*A61N 1/36* (2006.01)
*A61N 1/05* (2006.01)
*A61N 5/06* (2006.01)

(52) U.S. Cl.
CPC ....... *A61N 1/36139* (2013.01); *A61N 1/0529* (2013.01); *A61N 1/361* (2013.01);
(Continued)

(58) Field of Classification Search
CPC .................. A61N 1/36139; A61N 1/36062
(Continued)

(56) References Cited

U.S. PATENT DOCUMENTS

| 8,463,378 B2 | 6/2013 | Tass et al. |
| 9,884,164 B2 | 2/2018 | Tass et al. |
| 2011/0201977 A1* | 8/2011 | Tass ................. A61H 7/004 601/15 |

FOREIGN PATENT DOCUMENTS

| DE | 10 2006 052 078 A1 | 4/2010 |
| DE | 102009015723 A1 | 12/2010 |

(Continued)

OTHER PUBLICATIONS

I. Adamchic, C. Hauptmann, U. B. Barnikol, N. Pawelcyk, O.V. Popovych, T. Barnikol, A. Silchenko, J. Volkmann, G. Deuschl, W. Meissner, M. Maarout, V. Sturm, H.-J. Freund, P.A. Tass: Coordinated Reset Has Lasting Aftereffects in Patients with Parkinson's Disease. Movement Disorders 29, 1679 (2014).

(Continued)

*Primary Examiner* — Nadia A Mahmood
(74) *Attorney, Agent, or Firm* — Lowe Graham JOnes PLLC; Bruce E. Black (57) ABSTRACT

A device for stimulating neurons that includes a stimulation unit implantable in the body of a patient and having stimulation elements that stimulate neurons in the brain and/or spinal cord. A control unit controls the stimulation unit during first and second time intervals in different stimulation modes. The control unit controls the stimulation unit during 75% or more of the first time interval in the first stimulation mode to repeatedly generate sequences of stimuli and the order in which the stimulation elements generate stimuli is constant for not more than 5 successively generated sequences and then varied. The control unit controls the stimulation unit during 75% or more of the second time
(Continued)

interval in a second stimulation mode such that the stimulation elements repeatedly generate sequences of stimuli and the order in which the stimulation elements generate stimuli is constant for at least 25 successively generated sequences and then varied.

20 Claims, 5 Drawing Sheets

(52) U.S. Cl.
CPC ..... *A61N 1/36062* (2017.08); *A61N 1/36082* (2013.01); *A61N 5/0622* (2013.01); *A61N 2005/063* (2013.01); *A61N 2005/0612* (2013.01); *A61N 2005/0626* (2013.01)

(58) Field of Classification Search
USPC .......................................................... 607/2
See application file for complete search history.

(56) References Cited

FOREIGN PATENT DOCUMENTS

| DE | 102010016461 A1 | 10/2011 |
|---|---|---|
| DE | 102010016404 A1 | 12/2012 |

OTHER PUBLICATIONS

N. E. Huang et al.: A confidence limit for the empirical mode decomposition and Hilbert spectral analysis, Proceedings of the Royal Society of London Series A. 459, 2317-2345 (2003).

N. E. Huang et al.: The empirical mode decomposition and the Hilbert spectrum for nonlinear and non-stationary time series analysis. Proc. R. Soc, A: Math. Phys. Eng. Sci. 454:903-995 (1998).

P. A. Tass, L. Qin, C. Hauptmann, S. Doveros, E. Bezard, T. Boraud, W. G. Meissner: Coordinated reset neuromodulation has sustained after-effects in Parkinsonian monkeys. Annals of Neurology 72, 816-820 (2012).

P. A. Tass: Transmission of stimulus-locked responses in two coupled phase oscillators. Phys. Rev. E 69, 051909-1-24 (2004).

P. Temperli, J Ghika, J.-G. Villemure, P. Burkhard, J. Bogous-slavsky, and F. Vingerhoets: How do Parkinsonian signs return after discontinuation of subthalamic DBS? Neurology 60, 78 (2003).

PCT/EP2016/064471 International Search Report dated Sep. 16, 2016.

\* cited by examiner

DEVICE AND METHOD FOR EFFECTIVE INVASIVE TWO-STAGE NEUROSTIMULATION

CROSS-REFERENCE TO RELATED APPLICATIONS

This application is a National Stage entry of International Application No. PCT/EP2016/064471, filed on Jun. 22, 2016, which claims priority to German Application No. 10 2015 109 988.8, filed on Jun. 22, 2015, the contents of each of these priority applications are hereby incorporated by reference in their entirety.

TECHNICAL FIELD

The invention relates to an apparatus and to a method for effective invasive neurostimulation by means of varying stimulus sequences.

BACKGROUND

Nerve cell assemblies in circumscribed regions of the brain, e.g. of the thalamus and the basal ganglia, are pathologically, e.g. excessively synchronously, active in patients with neurological or psychiatric diseases such as Parkinson's disease, essential tremor, epilepsy, functional disturbances after a stroke, dystonia or obsessive compulsive disorders. In this case, a large number of neurons synchronously form action potentials, i.e. the participating neurons fire excessively synchronously. In a healthy person, in contrast, the neurons fire with a different quality, e.g. in an uncorrelated manner, in these brain sectors.

In Parkinson's disease, the pathologically synchronous activity changes the neuronal activity in other brain regions, e.g. in areas of the cerebral cortex such as the primary motor cortex. In this respect, the pathologically synchronous activity in the region of the thalamus and of the basal ganglia, for example, imposes its rhythm on the cerebral cortex areas such that ultimately the muscles controlled by these areas develop pathological activity, e.g. a rhythmic trembling (tremor).

Deep brain stimulation is used to treat Parkinson's patients who cannot be sufficiently treated by medication. In this process, deep electrodes are implanted in specific areas of the brain, e.g. in the subthalamic nucleus. An electrical stimulation is carried out via the deep electrodes to relieve the symptoms. With the standard high-frequency stimulation for treating Parkinson's disease, a so-called high frequency permanent stimulation is carried out at frequencies of more than 100 Hz. This kind of treatment has no long-lasting therapeutic effects (cf. P. Temperli, J. Ghika, J.-G. Villemure, P. Burkhard, J. Bogousslaysky, and F. Vingerhoets: How do Parkinsonian signs return after discontinuation of subthalamic DBS? Neurology 60, 78 (2003)). "Coordinated reset stimulation" (CR stimulation), that can additionally have long-lasting therapeutic effects, manages with less stimulation current (P. A. Tass, L. Qin, C. Hauptmann, S. Doveros, E. Bezard, T. Boraud, W. G. Meissner: Coordinated reset neuromodulation has sustained after-effects in Parkinsonian monkeys. Annals of Neurology 72, 816-820 (2012); I. Adamchic, C. Hauptmann, U. B. Barnikol, N. Pawelcyk, O. V. Popovych, T. Barnikol, A. Silchenko, J. Volkmann, G. Deuschl, W. Meissner, M. Maarouf, V. Sturm, H.-J. Freund, P. A. Tass: Coordinated Reset Has Lasting Aftereffects in Patients with Parkinson's Disease. Movement Disorders 29, 1679 (2014)).

With other diseases, e.g. epilepsy that cannot be sufficiently treated with medication, different electrodes, e.g. epicortical or epidural electrodes, are also implanted in addition to deep electrodes. With further diseases, e.g. chronic pain syndromes, it is customary to stimulate the spinal cord not only by means of deep electrodes in the brain, but also by means of e.g. epidural electrodes. In contrast to CR stimulation, most other types of stimulation have no long-lasting therapeutic effects.

Therapeutic effects can also be achieved by direct stimulation of the brain tissue or spinal cord by light, e.g. via implanted light-guides. Different spatiotemporal stimulation patters such as CR stimulation can also be used in this respect.

Although the deep brain stimulation by means of invasive CR stimulation enables long-lasting therapeutic effects, this approach has relevant limitations. The CR stimulation can cause side effects, e.g. due to the unwanted stimulation of adjacent structures as a result of the propagation of stimulation currents or due to the simultaneous stimulation, which is difficult to avoid for anatomical reasons, of e.g. fibrous webs and/or fibers that run in the vicinity of the target region or even through the target region. Such situations result e.g. due to the characteristic close anatomical proximity of the target point targeted in the electrode implantation and of other anatomic structures whose stimulation results in side effects, due to special individual anatomical conditions (e.g. in the sense of the location of blood vessels that have to be spared on the implantation of the electrodes) or also due to suboptimal or even erroneous electrode implantation.

Side effects caused by unfavorably positioned electrodes only disappear when the stimulation level is reduced so much that the desired effects do not occur to a sufficient degree or do not even occur at all. Analogously, an insufficient stimulation effect cannot be compensated by an increase in the stimulation intensity by any desired amount since hereby side effects typically occur or even damage to the tissue is caused.

Where necessary, badly positioned electrodes or other stimulation means have to be re-implanted to position them such that the treatment is efficient. A repeat implantation is always associated with a risk, e.g. due to the risk of an injury to vessels or due to an infection.

SUMMARY

It is the underlying object of the invention to provide an apparatus and a method for stimulating neurons with which robust therapeutic effects can be achieved despite a reduced stimulus level and without a significantly increased stimulation time.

The object underlying the invention is satisfied by the features of the independent claims. Advantageous further developments and aspects of the invention are set forth in the dependent claims.

BRIEF DESCRIPTION OF THE DRAWINGS

The invention will be described in more detail in the following in an exemplary manner with reference to the drawings. There are shown in these.

DETAILED DESCRIPTION

Figure 1:
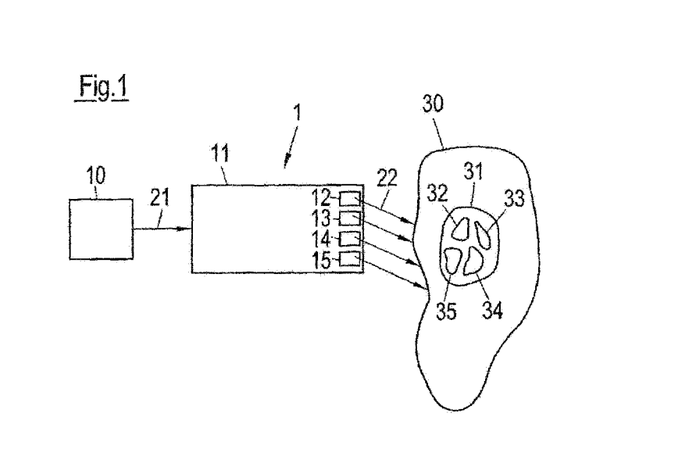
FIG. 1 illustrates a schematic representation of an apparatus for suppressing a pathologically synchronous and oscillatory neuronal activity and in particular for desynchronizing neurons having a pathologically synchronous and oscillatory activity in accordance with a first embodiment.

An apparatus 1 for stimulating neurons having a pathologically synchronous and oscillatory neuronal activity is shown schematically in FIG. 1. The apparatus 1 comprises a control unit 10 and a stimulation unit 11 that has a plurality of stimulation elements. Four stimulation elements 12, 13, 14 and 15 are shown by way of example in FIG. 1. The stimulation unit 11 can naturally, however, also have a different number of stimulation elements, for example 2, 3, 5, 6, etc. In the case of electrical stimulation, the stimulation elements 12 to 15 can e.g. be stimulation contact surfaces of one or more electrodes for applying electrical stimuli. If stimulation takes place optically, light guides can e.g. be used as the stimulation elements 12 to 15 to stimulate the neuronal tissue with light stimuli at the desired points.

During the operation of the apparatus 1, the control unit 10 carries out a control of the stimulation unit 11. For this purpose, the control unit 10 generates control signals 21 which are received by the stimulation unit 11.

The stimulation unit 11 is surgically implanted in the body of the patient and generates stimuli 22 on the basis of the control signals 21, in particular electrical and/or optical stimuli 22, which are administered to the brain and/or to the spinal cord 30 of the patient. The stimuli 22 are adapted to suppress the pathologically synchronous and oscillatory neuronal activity on administration to the patient and in particular to desynchronize the neurons having the pathologically synchronous and oscillatory activity.

The control unit 10 can be a non-invasive units, i.e. it is located outside the body of the patient during the operation of the apparatus 1 and is not surgically implanted in the body of the patient.

The apparatus 1 and the apparatus 2 described further below in connection with FIG. 4 can in particular be used for treating neurological or psychiatric diseases, e.g. Parkinson's disease, essential tremor, tremor resulting from multiple sclerosis as well as other pathological tremors, dystonia, epilepsy, depression, locomotor disorders, cerebellar diseases, obsessive compulsive disorders, dementia, Alzheimer's, Tourette's syndrome, autism, functional disorders after stroke, spasticity, tinnitus, sleep disorders, schizophrenia, irritable bowel syndrome, addiction diseases, borderline personality disorder, attention deficit syndrome, attention deficit hyperactivity syndrome, pathological gambling, neuroses, bulimia, anorexia, eating disorders, burnout syndrome, fibromyalgia, migraine, cluster headache, general headache, neuralgia, ataxia, tic disorder or hypertension as well as further diseases which are characterized by pathologically increased neuronal synchronization.

The aforesaid diseases can be caused by a disorder of the bioelectrical communication of neuronal assemblies which are connected in specific circuits. In this respect, a neuronal population continuously generates pathological neuronal activity and possibly a pathological connectivity associated therewith (network structure). In this respect, a large number of neurons synchronously form action potentials, i.e. the participating neurons fire excessively synchronously. In addition, there is the fact that the pathological neuronal population has an oscillatory neuronal activity, i.e. the neurons fire rhythmically. In the case of neurological or psychiatric diseases, the mean frequency of the pathological rhythmic activity of the affected neuronal assemblies lies approximately in the range from 1 to 30 Hz, but can also be outside this range. In healthy people, the neurons fire qualitatively differently, however, e.g. in an uncorrelated manner.

The apparatus 1 is shown during a CR stimulation in FIG. 1. At least one neuronal population 31 in the brain and/or spinal cord 30 of the patient has a pathologically synchronous and oscillatory neuronal activity as described above. The stimulation unit 11 stimulates the pathologically active neuronal population 31 in the brain and/or spinal cord 30 with the electrical and/or optical stimuli 22 either directly or the stimuli 22 are forwarded via the nervous system to the pathologically active neuronal population 31. The stimuli 22 are designed such that the time-delayed (or phase-shifted) stimulation having at least two stimulation elements effects a desynchronization of the pathologically synchronous activity of the neuronal population 31. A lowering of the coincidence rate of the neurons effected by the stimulation can result in a lowering of the synaptic weights and thus in an unlearning of the tendency to produce pathologically synchronous activity.

The stimuli 22 administered in the CR stimulation effect a reset of the phase of neuronal activity of the stimulated neurons in the neuronal population 30. The phase of the stimulated neurons is set to or close to a specific phase value, e.g. 0°, independently of the current phase value by the reset (it is not possible in practice to set a specific phase value exactly; however, this is also not required for a successful CR stimulation). The phase of the neuronal activity of the pathological neuronal population 31 is thus controlled by means of a direct stimulation. Since the pathological neuronal population 31 is stimulated at different points via the stimulation elements 12 to 15, the respective phases of the neuronal activity of the subpopulations 32 to 35 of the pathological neuronal population 31 shown in FIG. 1 are reset at different points in time in that the stimuli 22 are applied in a time-delayed (or phase-shifted) manner by the stimulation elements 12 to 15. As a result, the pathological neuronal population 31 whose neurons were previously active synchronously and at the same frequency and phase are split into a plurality of subpopulations having different phases. The stimulation element 12, for example, stimulates the subpopulation 32; the stimulation element 13 stimulates the subpopulation 33; the stimulation element 14 stimulates the subpopulation 34; and the stimulation element 15 stimulates the subpopulation 35. The neurons are still synchronous and also still fire at the same pathological frequency within each of the subpopulations 32 to 35 after the reset of the phase; however, each of the subpopulations 32 to 35 has that phase with respect to their neuronal activity that was imparted on them by the stimulus 22 generated by the respective stimulation element 32 to 35. This means that the neuronal activities of the individual subpopulations 32 to 35 still have an approximately sinusoidal curve at the same pathological frequency, but different phases, after the resetting of their phases.

As described above, the stimulation elements 12 to 15 stimulate different subpopulations with the stimuli 22. In this respect, however, it does not necessarily have to be a case of disjunctive subpopulations, i.e. subpopulations completely separate from one another. The subpopulations stimulated by the stimulation elements 12 to 15 can also overlap one another.

Due to the pathological interaction between the neurons, the state with at least two subpopulations generated by the stimulation is unstable and the total neuronal population 31 fast approaches a state of complete desynchronization in which the neurons fire without correlation. The desired state i.e. the complete desynchronization is thus not immediately present after the time-offset (or phase-shifted) application of the stimuli 22, but is usually adopted within a few periods or even in less than one period of the pathological frequency.

One theory for explaining the stimulation success is based on the fact that the ultimately desired desynchronization is only made possible by the pathologically increased interaction between the neurons. In this respect, a self-organization process is made use of which is responsible for the pathological synchronization. It also has the effect that a division of an overall population 31 into subpopulations 32 to 35 with different phases is followed by a desynchronization. In contrast to this, no desynchronization would take place without a pathologically increased interaction of the neurons.

Furthermore, a reorganization of the connectivity of the disturbed neuronal networks can be achieved by the CR stimulation so that long-continuing therapeutic effects can be brought about. The obtained synaptic conversion is of great importance for the effective treatment of neurological or psychiatric diseases.

In CR stimulation, the stimuli 22 are typically applied at different sites of the brain and/or of the spinal cord 30 at different times as part of a so-called sequence. Stimulation is carried out exactly once at each of the different stimulation sites in a sequence, i.e. each of the subpopulations 32 to 35 is stimulated exactly once within a sequence in the above example. CR stimulation with a slow-varying sequence of the CR stimulation is superior over a wide range of stimulus levels to CR stimulation with a fixed sequence or with a sequence varying quickly, e.g. from stimulation cycle to stimulation cycle. In the range of very small stimulus levels, CR stimulation does not produce any long-lasting therapeutic effects, independently of whether and how the sequence is varied.

If CR stimulation is applied with a fast-varying sequence at a very low stimulus level, a desynchronizing effect occurs under stimulation that typically does not last long after the end of the stimulation, however. With CR stimulation with a fixed or a slow-varying sequence, typically no desynchronizing effect occurs at very low stimulation levels, neither during nor after the stimulation.

The invention is based on the following surprising observation: An epoch with a desynchronizing stimulation with a fast-varying sequence admittedly per se does not have any long-lasting desynchronizing effect at a low stimulation level, but in combination with an epoch with a desynchronizing stimulation with a slow-varying sequence of a high stimulus level, it effects a long-lasting desynchronizing effect that is at least equal to or even significantly better than the effect achieved by two consecutive epochs with a desynchronizing stimulation (with a fixed, fast-varying or slow-varying sequence) at the higher stimulus level.

The invention consequently uses a two-stage stimulation in which stimulation takes place in the first stage with a fast-varying sequence at a low stimulus level and in the second stage with a slow-varying sequence at a higher stimulus level. The stimulation unit 11 can be operated in two different stimulation modes (or operating modes) to implement the two stages. The control unit 10 operates the stimulation unit 11 in a first stimulation mode during at least 75% of the time of a first time interval. In the first stimulation mode, the control unit 10 controls the stimulation unit 11 such that the stimulation elements 12 to 15 repetitively generate sequences of stimuli 22 and the order in which the stimulation elements 12 to 15 generate the stimuli 22 within a sequence is constant for at most 5 consecutively generated sequences and is then varied, with the level of the stimuli 22 in the first stimulation mode being smaller than or equal to a predefined stimulus level. A second time interval follows the first time interval. The second time interval can in particular be directly subsequent to the first time interval, i.e. without a break therebetween. The control unit 10 operates the stimulation unit in the second stimulation mode during at least 75% of the time of the second time interval. In the second stimulation mode, the control unit 10 controls the stimulation unit 11 such that the stimulation elements 12 to 15 repetitively generate sequences of stimuli 22 and the order in which the stimulation elements 12 to 15 generate the stimuli 22 within a sequence is constant for at least 25 consecutively generated sequences and is then varied. The level of the stimuli 22 in the second stimulation mode amounts to at least 1.3 times the predefined stimulus level.

The above-described stimulation form is sufficiently robust that it is sufficient for the desired stimulation success when the stimulation unit 11 is operated in the first stimulation mode for only 75% of the time of the first time interval and is operated in the second stimulation mode for only 75% of the time of the second time interval. The operating times of the first and second stimulation modes in the respective time intervals can naturally also be increased. For example, the stimulation unit 11 can be operated in the first stimulation mode during the complete first time interval and can be operated in the second stimulation mode during the complete second time interval. During time periods in which the stimulation unit 11 is not operated in the first stimulation mode during the first time interval or is not operated in the second stimulation mode during the second time interval, either no stimulation can take place or a stimulation can take place that can in particular be different than the stimulation described in this application.

Figure 2:
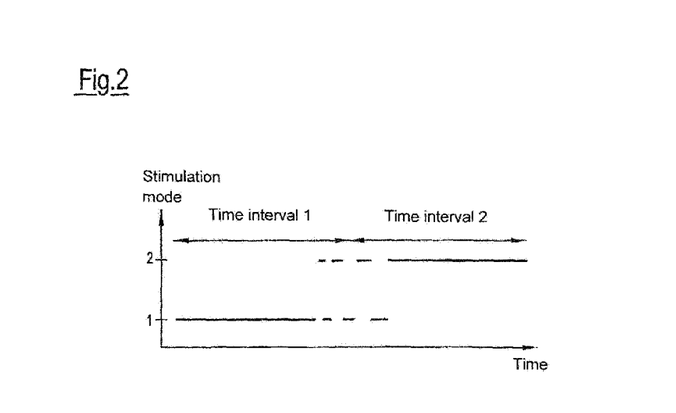
FIG. 2 illustrates a schematic representation of a fractionated transition from a first stimulation mode into a second stimulation mode.

It can be advantageous for the patient not to carry out the change from the first stimulation mode into the second stimulation mode abruptly, but rather in a fractionated manner, such as is shown by way of example in FIG. 2. An abrupt change from a stimulation level below threshold in the first stimulation mode to a stimulation level above threshold in the second stimulation mode can be very unpleasant, e.g. painful. To make this transition more pleasant, familiarization effects can be used in that a switch is made to and fro between the two stimulation modes as part of the transition from the first time interval to the second time interval. The degree of the side effects, e.g. pain, does not only depend on the stimulation level, but also on the duration of the stimulus application. The start of side effects can be considerably weakened by applying short epochs in the second stimulation mode. Familiarization effects can even occur so that the side effects in the second stimulation mode later applied over a long period are smaller than without the fractionated transition. The duration between the switching to and from between the first and second stimulation modes can vary in time as part of the transmission and can e.g. increase as is shown by way of example in FIG. 2.

Figure 3A:
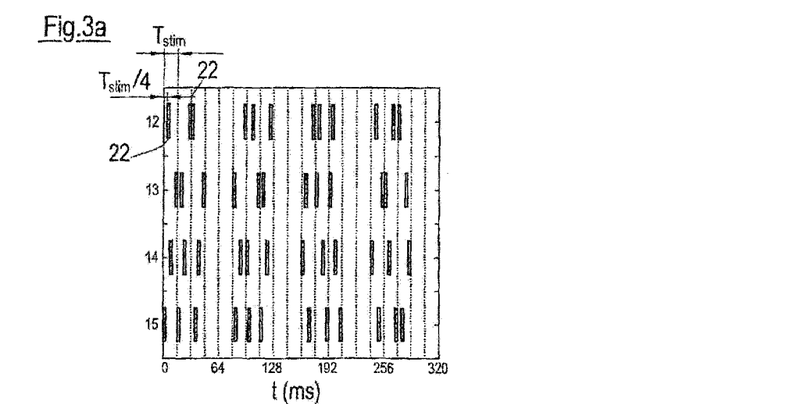
FIG. 3A illustrates a schematic representation of a CR stimulation with fast-varying stimulus sequences.
Figure 3B:
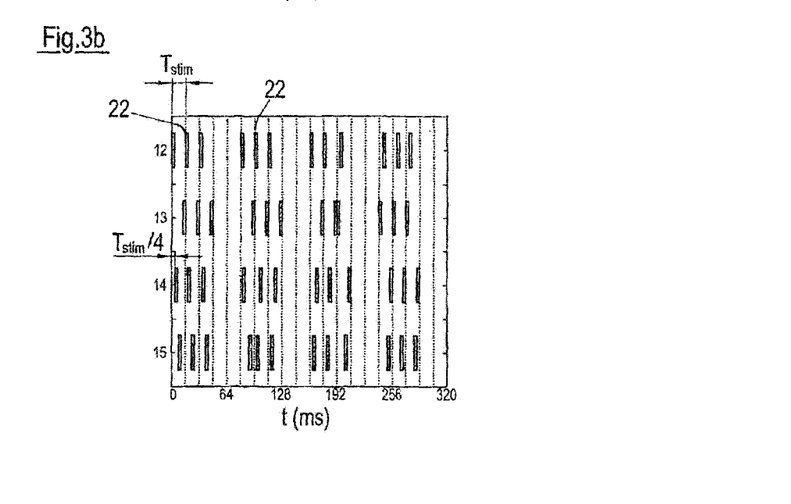
FIG. 3B illustrates a schematic representation of a CR stimulation with slow-varying stimulus sequences.

Embodiments for stimulations in the first and second stimulation modes are shown in FIGS. 3A and 3B.

FIG. 3A shows a CR stimulation in which the four stimulation elements 12 to 15 repetitively generate fast-varying sequences of stimuli 22 in the first stimulation mode. The stimuli 22 generated by the stimulation elements 12 to 15 are applied among one another against the time t in FIG. 3A. The sequences are generated in a predefined time pattern that comprises consecutive cycles. The individual cycles are delineated from one another by dashed lines in FIG. 3A. Each cycle has the length $T_{stim}$. In each cycle in which a stimulation takes place, the stimulation elements 12 to 15 generate exactly one sequence of stimuli 22 and each stimulation element 12 to 15 generates exactly one stimulus 22, i.e. each sequence in the present example comprises a progression of four time-delayed stimuli 22 that are in particular generated in respectively different stimulation channels 12 to 15, wherein the time delay can in particular relate to the starting times of the stimuli 22. The order in which the stimulation elements 12 to 15 generate the stimuli 22 varies at the start of each cycle in the present example. A different filling of the bars shown in FIG. 3A that symbolize the stimuli 22 shows a variation of the order. The stimulation elements 12 to 15, for example, generate the stimuli 22 in the order 15-12-14-13 in the first cycle shown in FIG. 3A. The order in the second cycle is 15-13-14-12 and the order in the third cycle is 12-15-14-13.

Provision can be made, as described above, that the sequences only remain the same for a maximum of 5 sequences generated after one another and are then changed. The variation of the sequences can furthermore take place with a constant rhythm, i.e. a variation always takes place, for example, after $i_{Mode\_1}$ cycles, where $i_{Mode\_1}$ is a whole number from 1 to 5. Alternatively, the number of cycles after which the sequence is varied can be determined in accordance with stochastic or deterministic rules or mixed stochastic-deterministic rules.

In accordance with an embodiment, only the order in which the stimulation elements 12 to 15 generate the stimuli 22 per sequence is varied in the CR stimulation shown in FIG. 3B. All the other stimulation parameters can remain constant during the CR stimulation.

The variation of the sequences can e.g. take place stochastically or deterministically or in a mixed stochastic-deterministic manner.

Provision can be made that the CR stimulation takes place continuously in the first stimulation mode, i.e. sequences of stimuli 22 are always generated in consecutive cycles. Alternatively, breaks can, however, also be observed during the CR stimulation, in particular during whole cycles. Stimuli 22 can thus be generated during $n_{Mode\_1}$ consecutive cycles and, during the following $m_{Mode\_1}$ cycles, no stimuli 22 are generated that are designed to desynchronize the pathologically synchronous and oscillatory neuronal activity, where $n_{Mode\_1}$ and $m_{Mode\_1}$ are non-negative whole numbers. The pattern of $n_{Mode\_1}$ cycles with stimulation and $m_{Mode\_1}$ cycles without stimulation can be periodically continued. $n_{Mode\_1}=3$ and $m_{Mode\_1}=2$ apply to the exemplary stimulation form shown in FIG. 3A.

It is conceivable that different stimuli that are not adapted to suppress pathologically synchronous and oscillatory neuronal activity are applied during the stimulation breaks, in particular using the stimulation unit 11. Alternatively, the stimulation unit 11 does not generate any stimuli during the stimulation breaks.

Provided that provision is made to vary the sequences after a predefined number $i_{Mode\_1}$ of sequences ($i_{Mode\_1} \geq 5$), in accordance with an embodiment, the cycles without any stimulation are not counted, i.e. in this embodiment, a variation of the order in which the stimulation elements 12 to 15 generate the stimuli 22 only takes place when a respective sequence of stimuli 22 was actually applied in $i_{Mode\_1}$ cycles.

Each of the four stimulation elements 12 to 15 stimulates a respective one of the subpopulations 32 to 34 of the pathological neuron populations 31 shown in FIG. 1. During the maximum of 5 cycles in which the sequences are constant, the stimulus 22 is periodically applied with the period $T_{stim}$ by each of the stimulation elements 12 to 15. The stimuli 22 effect a phase reset of the neuronal activity of the respective stimulated subpopulation. The time delay between stimuli 22 generated directly after one another by different stimulation elements within a sequence furthermore amounts to $T_{wtim}/4$ since, in the present embodiment, four stimulation elements 12 to 15 are used for the CR stimulation. For the general case of P stimulation elements used for the stimulation, the time delay between stimuli 22 generated directly after one another by different stimulation elements within a sequence would amount to $T_{stim}/P$ (a deviation from this value by e.g. up to ±5%, ±10% or ±20% is also possible). The time delay $T_{stim}/P$ can relate to the initial points in time of the stimuli 22. The stimuli 22 generated by different stimulation elements can be identical except for the different starting times.

The period $T_{stim}$ that indicates the duration of a cycle, on the one hand, and the period with which unchanging sequences and the stimuli 22 generated by a respective stimulation element 12 to 15 are repeated, on the other hand, can be close to the mean period of the pathological oscillation of the neuronal population 31 with the pathologically synchronous and oscillatory neuronal activity or can differ from the mean period by up to ±5%, ±10% or ±20%. The frequency $f_{stim}=1/T_{stim}$ is typically in the range from 1 to 30 Hz. The period of the pathological oscillation of the neuronal population 31 to be stimulated can be measured by means of EEG, for example. It is, however, also possible to use text book values or empirical values that relate to the respective disease to be treated for the period of the pathological oscillation.

The phase-resetting stimuli 22 can, for example, be individual stimuli or also assembled stimuli. Each stimulus 22 can, for example, comprise a pulse train of 2 to 100, in particular 2 to 10, individual pulses. The individual pulses within a pulse train are repeated without interruption at a frequency in the range from 50 to 500 Hz, in particular in the range from 100 to 150 Hz. The pulses of a pulse train can be identical.

The level of the stimuli 22, i.e. the amplitude of the stimuli 22, is smaller than or equal to a predefined stimulus level in the first stimulation mode. The pre-defined stimulus level can in particular be sub-threshold in the sense that the stimuli 22 only have desynchronizing effects during the stimulation, but do not outlast the end of the stimulation, i.e. after the end of the stimulation by the stimuli 22 whose stimulation level does not exceed the predefined stimulus level the desynchronizing effect disappears.

The stimulation unit 11 can generally include any desired number L of stimulation elements ($L \geq 2$), but all L stimulation elements do not necessarily have to be used in a stimulation; for example, only a selection of P or L stimulation elements can also generate the stimuli 22 (2≤P≤L). With P stimulation elements, P! possible different sequences result, with each of the P stimulation elements generating exactly one stimulus 22 in each of these sequences. It is conceivable to use all P! possible sequences for the stimulation or to select a subset for the stimulation from the set of P! possible sequences. This subset can also vary in time in accordance with stochastic or deterministic or mixed stochastic-deterministic rules. The progression of the sequences can be random or can be fixed before the start of the stimulation or also during the stimulation.

The neuronal population 31 is brought into a state by the stimulation in the first stimulation mode in which it is considerably more receptive for the following stimulation in the second stimulation mode with a slow-varying sequence and a higher stimulus level.

The stimulation in the second stimulation mode can, with the exception of the number of cycles after which the sequence is varied and the stimulus level, can have the same configurations as the stimulation explained above in connection with FIG. 3A in the first stimulation mode. The differences of the stimulation in the second stimulation mode with respect to the stimulation in the first stimulation mode will be explained with reference to FIG. 3B in the following.

FIG. 3B shows a CR stimulation in which the four stimulation elements 12 to 15 repetitively generate slow-varying sequences of stimuli 22 in the second stimulation mode. The order in which the stimulation elements 12 to 15 generate the stimuli 22 within one sequence is kept constant for at least 25 sequences generated after one another and is only then varied. It is furthermore conceivable to increase the repetition of the same sequence and to keep the order in which the stimulation elements 12 to 15 generate the stimuli 22 per cycle constant for at least 30 or at least 35 consecutively generated sequences, for example, in the second stimulation mode. It must again be pointed out at this point that the sequences are already varied after fewer than 25 sequences in FIG. 3B for reasons of illustration. This is, however, only to be understood as a simplified representation of a sequence variation slow in comparison with FIG. 3A.

The variation of the sequences in the second stimulation mode can take place at a constant rhythm, i.e. a variation always takes place after $i_{Mode\_2}$ cycles, where $i_{Mode\_2} \geq 25$ applies. Alternatively, the number of cycles after which the sequence is varied can be determined in accordance with stochastic or deterministic rules or mixed stochastic-deterministic rules.

As in the stimulation in the first stimulation mode, only the order in which the stimulation elements 12 to 15 generate the stimuli 22 per sequence can also be varied in the stimulation in the second stimulation mode. All the other stimulation parameters can remain constant during the stimulation.

The variation of the sequences can e.g. take place stochastically or deterministically or in a mixed stochastic-deterministic manner.

The CR stimulation can take place continuously in the second stimulation mode, i.e. sequences of stimuli 22 are always generated in consecutive cycles.

Alternatively, breaks can, however, also be observed during the CR stimulation, in particular during whole cycles. Stimuli 22 can thus be generated during $n_{Mode\_2}$ consecutive cycles and, during the following $m_{Mode\_2}$ cycles, no stimuli 22 are generated that are designed to desynchronize the pathologically synchronous and oscillatory neuronal activity, where $n_{Mode\_2}$ and $m_{Mode\_2}$ are non-negative whole numbers. The pattern of $n_{Mode\_2}$ cycles with stimulation and $m_{Mode\_2}$ cycles without stimulation can be periodically continued. $n_{Mode\_2}=3$ and $m_{Mode\_2}=2$ apply to the exemplary stimulation form shown in FIG. 3B. The values for $n_{Mode\_2}$ and $m_{Mode\_2}$ of the second stimulation mode can be, but do not have to be, identical to the values for $n_{Mode\_2}$ or $m_{Mode\_2}$ of the first stimulation mode.

It is conceivable that different stimuli that are not adapted to suppress pathologically synchronous and oscillatory neuronal activity are applied during the stimulation breaks, in particular using the stimulation unit 11. Alternatively, the stimulation unit 11 does not generate any stimuli during the stimulation breaks.

Provided that provision is made to vary the sequences after a predefined number $i_{Mode\_2}$ of sequences ($i_{Mode\_2} \geq 25$), in accordance with an embodiment, the cycles without any stimulation are not counted, i.e. in this embodiment, a variation of the order in which the stimulation elements 12 to 15 generate the stimuli 22 only takes place when a respective sequence of stimuli 22 was actually applied in $i_{Mode\_2}$ cycles.

The level of the stimuli 22, i.e. the amplitude of the stimuli 22, amounts to at least 1.3 times that of the predefined stimulus level in the second stimulation mode. The level of the stimuli 22 can in particular be so large that a pronounced and long-lasting therapeutic and/or desynchronizing effect would be achieved if the stimuli 22 were to be applied during the total stimulation time, i.e. during the first and second time periods. In accordance with an embodiment, the lower limit for the stimulus level in the second stimulation mode is greater than 1.3 times the predefined stimulus level and amounts to 1.5 times or 1.7 times the predefined stimulus level. If the stimuli 22 are electrical current-controlled stimuli 22, the stimulus level is given the by current of the stimuli 22. In the case of optical stimuli 22, the stimulus level can be the luminous intensity of the stimuli 22.

In the two-stage stimulation described here, the stimulus level is metered up without loss or restriction of effectiveness. During the first stage, i.e. in the first stimulation mode, a sub-threshold stimulus level is sufficient, whereby unwanted effects can be considerably reduced. The neuronal population 31 is brought into a state by the stimulation in the first stimulation mode in which it is considerably more receptive for the stimulation subsequently carried out in the second stage in the second stimulation mode. The two-stage stimulation consequently enables an improved stimulation effect with simultaneously reduced side effects and other unwanted effects.

The underlying principle of the two-stage stimulation, namely the amplification of the desynchronizing effect of the stimulation with a slow-varying sequence by an upstream stimulation with a fast-varying sequence, does not only apply on a sub-threshold stimulus level of the stimulation with a fast-varying sequence. The effect of the two-stage stimulation rather at least tends to be better with a supra-threshold first stage than all other variants of CR stimulation of the same intensity and duration. However, for the case of the first stage with a supra-threshold stimulus level, the particular advantage is omitted that side effects and other unwanted effects can be avoided or at least reduced by the use of the sub-threshold stimulation.

The apparatus 1 shown in FIG. 1 for stimulating neurons with a pathologically synchronous and oscillatory neuronal activity carries out a so-called "open-loop" stimulation, i.e.

a stimulation without sensors that are used for feedback and/or for control of the stimulation.

Figure 4:
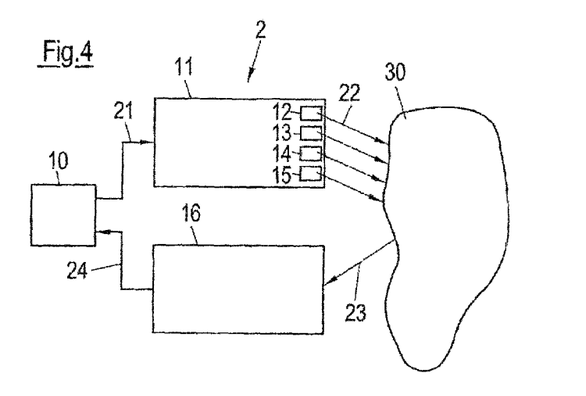
FIG. 4 illustrates a schematic representation of an apparatus for suppressing a pathologically synchronous and oscillatory neuronal activity and in particular for desynchronizing neurons having a pathologically synchronous and oscillatory activity in accordance with a second embodiment.

FIG. 4 schematically shows an apparatus 2 for stimulating neurons with a pathologically synchronous and oscillatory neuronal activity with which a closed-loop stimulation can be carried out. The apparatus 2 is a further development of the apparatus 1 shown in FIG. 1 and, exactly like the apparatus 1, includes a control unit 10 and an implantable stimulation unit 11 that have the same functions and properties as the above-described control and stimulation units 10, 11 of the apparatus 1.

The apparatus 2 furthermore comprises a measuring unit 16. The stimulation effect achieved by the stimuli 22 is measured with the aid of the measuring unit 16. The measuring unit 16 records one or more measured signals 23 measured at the patient, converts them as required into electrical signals 24 and supplies them to the control unit 10. The neuronal activity in the stimulated target zone or in a zone associated with the target zone can in particular be measured by means of the measuring unit 16, with the neuronal activity of this zone correlating sufficiently closely with the neuronal activity of the target zone. A non-neuronal activity, e.g. a muscular activity, or the activation of the autonomous nervous system can also be measured by means of the measuring unit 16 provided that they are sufficiently closely correlated with the neuronal activity of the target region.

The measuring unit 16 includes one or more sensors that in particular make it possible to demonstrate a decrease or increase in the amplitude of the pathological oscillatory activity.

Non-invasive sensors can be used as the sensors, e.g. chronically or intermittently used electroencephalography (EEG) electrodes or electromyography (EMG) electrodes or magnetoencephalography (MEG) sensors. The neuronal activity can also be determined by detection of characteristic movement patterns such as tremor, akinesia, or epileptic fits with the aid of an accelerometer or gyroscope or indirectly by measuring the activation of the autonomous nervous system by means of a measurement of the skin resistance. Mental state values that can be input into portable devices, e.g. smartphones, by the patient can also be used to monitor the stimulation success. Such mental state values can also be determined using short questionnaires.

Alternatively, the sensors can be implanted in the body of the patient. Epicortical electrodes, deep brain electrodes for the measurement of e.g. local field potentials, subdural or epidural brain electrodes, subcutaneous EEG electrodes and subdural or epidural spinal cord electrodes can, for example, serve as invasive sensors. The deep electrodes for measuring the local field potentials can also be combined construction-wise or can even be identical to the deep electrodes used for the stimulation.

The control unit 10 processes the signals 24, e.g. the signals 24 can be amplified and/or filtered, and analyzes the processed signals 24. The control unit 10 checks the stimulation success using the measured signals 23 recorded in response to the application of the stimuli 22.

As soon as a pronounced desynchronization or acute improved clinical findings or an pronounced improvement of the mental state of the patient has in particular been determined with reference to the measured signals 23 recorded by the measuring unit 16, a switchover can be made, in particular with the aid of the control unit 10, from the first stimulation mode into the second stimulation mode. An input unit coupled to the control unit 10 can in particular be provided which can be operated by the patient and/or by the treating physician and by which a switchover can be made from the first stimulation mode into the second stimulation mode.

The stimulation success can in particular be checked by means of a threshold value comparison. Depending on which signals are used for determining the stimulation success, different threshold value comparisons result. If e.g. the pathologically neuronal synchronization is measured via the sensors of the measuring unit 16, e.g. EEC electrodes or deep electrodes (as an LFP signal), experience has shown that the lowering of the synchronization by a predefined value, e.g. by at least 20% in comparison with the situation without stimulation, is sufficient to determine a sufficient stimulation success and to change from the first stimulation mode into the second stimulation mode. Larger values, e.g. 50% and more, can, however, be selected to stimulate for longer in the first stimulation mode and thus at a lower stimulus level.

The clinical improvement in findings is determined using typical changes of clinical cores or questionnaires familiar to the skilled person. For this purpose, the values known from text books e.g. delta S for a "minimally clinically relevant change" or also larger values such as 2×delta S are used.

In addition to the above-described regulation that determines the switchover from the first stimulation mode into the second stimulation mode, a further regulation can be provided that acts on a slower time scale. If a therapeutic success has taken place over a predetermined time period, e.g. 1 hour, the stimulation is switched off. The therapeutic success is measured as described above in this process, with the threshold values for a sufficient therapeutic success being able to be preset by the user, e.g. a lowering of the initial synchronization by 80%. If these threshold values are exceeded again for a predefined time period, e.g. 60 s, and/or if the patient reports a no longer sufficiently improved mental state, the two-stage stimulation is restarted as described above.

Values for the lengths of the first time interval and of the second time interval that are required to achieve the desired stimulation success can be estimated for a respective patient with the aid of the measuring unit 16. Subsequently, this information can be used for an application with the apparatus 1 that has no measuring unit. In general, the lengths of the first and second time intervals can be in the minute or hour range.

The predefined stimulus level from which the upper and lower limits for the stimulus levels are produced in the first and second stimulation modes can furthermore be determined with the aid of the measuring unit 16 in accordance with an embodiment. This information can also subsequently be used in an application with the apparatus 1. To determine the predefined stimulus level, the stimulation unit 11 is e.g. operated in the first stimulation mode and the level of the stimuli 22 is increased for so long, starting from zero, until an acute effect is adopted, i.e. a reduction of the synchronization of the stimulated neuronal population 31 that, however, disappears again after the end of the stimulation. The predefined stimulus level can be derived from the stimulus level acquired in this manner in that the predefined stimulus level is, for example, selected from a range whose lower level represents the stimulus level in which a reduction of the synchronization of the stimulated neuronal population starts and whose upper limit is e.g. 1.1 times the above stimulus level.

The individual components of the apparatus 1 and 2, in particular the control unit 10, the stimulation unit 11 and/or the measuring unit 16, can be separate from one another in a construction aspect. The apparatus 1 and 2 can therefore also be understood as systems. The control unit 10 can include a processor, e.g. a microcontroller, for carrying out its work. The stimulation process described herein can be stored as software code in a memory associated with the control unit 10.

The stimulation unit 11 can e.g. be a brain pacemaker and in this case has one or more implantable electrodes, e.g. deep electrodes, as well as optionally connection cables connected therebetween. The electrodes of the stimulation unit 11 typically comprise an insulated electrode shaft and a plurality of stimulation contact surfaces which have been introduced into the electrode shaft.

Figure 5:
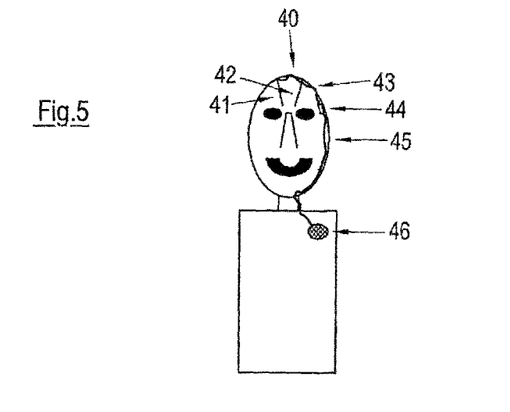
FIG. 5 illustrates a schematic illustration of an apparatus for the electrical stimulation of neurons having a pathologically synchronous and oscillatory neuronal activity.

FIG. 5 schematically shows an apparatus 40 for invasive electrical stimulation of neurons having a pathologically synchronous and oscillatory neuronal activity in accordance with an embodiment of the invention. The apparatus 40 comprises two electrodes 41, 42 that are implanted in the brain of the patient and are connected to a connector 44 via cables. The connector 44 is in turn connected to a control unit 46 via a cable 45. The apparatus 40 can have the functions of the above-described apparatus 1 and 2.

Implantable stimulation units for the optical stimulation of neuronal tissue are known. For example a light source such as a laser, a laser diode or an LED can generate a light beam that is distributed with the help of a light coupling to the inputs of a fiber bundle comprising a plurality of light guides. In this process, a control unit predefines e.g. the point in time at which an individual light pulse or a series of light pulses is coupled into which fiber of the fiber bundle. The decoupling points of the individual fibers of the fiber bundle, i.e. the end of the fibers, lie at different points in the target region in the brain or spinal cord of the patient. The light thus stimulates different sites of the target region in a time sequence predefined by the control unit. Different implantable stimulation units can, however, also be used that are suitable for a direct optical stimulation of neuronal tissue.

As described above, the stimuli 22 effect a reset of the phase of the neuronal activity of the stimulated neurons in the CR stimulation. The phase reset of the individual stimuli 22 can be checked with the aid of the measured signals 23 recorded by the measuring unit 16. Such an examination can be carried out before the actual two-stage therapeutic neurostimulation.

For this purpose, a signal that sufficiently represents the activity of the subpopulation stimulated over the jth stimulation channel is measured via a sensor of the measuring unit 16. This signal is obtained either directly from the subpopulation via a non-invasive measurement, e.g. via EEG or MEG electrodes, or via an invasive measurement, e.g. via implanted electrodes, as a surface EEG or as a local field potential via deep electrodes. The signal can also be determined indirectly via the measurement of a value correlated with the activity of the stimulated subpopulation. EEG/MEG/LFP signals of the neuronal activity of a different neuronal population tightly coupled to this subpopulation are e.g. suitable for this purpose or associated electromyography signals, accelerometer signals or gyroscope signals.

Since neuronal signals typically include rhythmic activity in different frequency bands, it is advantageous in such cases to determine the signal $x_j(t)$ that represents the pathological oscillatory activity of the subpopulation stimulated by the jth stimulation channel, e.g. by means of band pass filtering or wavelet analysis or empirical mode decomposition.

A procedure that is only a little complex to check a phase reset comprises determining the averaged stimulus response. A stimulus having identical stimulus parameters is applied at the times $T_1, T_2, \ldots, T_I$ for this purpose. The intervals between the individual stimuli $T_{k+1}-T_k$ should be sufficiently large and randomized, that is should not be constant, in order to avoid transient effects (cf. P A. Tass: Transmission of stimulus-locked responses in two coupled phase oscillators. Phys. Rev. E 69, 051909-1-24 (2004)). The intervals $T_{k+1}-T_k$ should typically be in the range of at least tenfold, preferably a hundredfold the mean period of the pathological oscillation. The stimulus response averaged over all I test stimuli is calculated in accordance with the following equation:

$$\bar{x}_j(t) = \frac{1}{I}\sum_{k=1}^{I} x_j(\tau_k + t) \tag{1}$$

Provided that the intervals $T_{k+1}-T_k$ between the individual stimuli are sufficiently large, no averaged stimulus response is obtained in the pre-stimulus range, i.e. in the range before the application of a respective stimulus (cf. P A. Tass: Transmission of stimulus-locked responses in two coupled phase oscillators. Phys. Rev. E 69, 051909-1-24 (2004)). A phase reset can be determined when an averaged stimulus response can be detected, i.e. when a stimulus response different from zero is found in the post-stimulus range, i.e. in the range for t>0, where t=0 is the starting time of the respective stimulus. This can be determined by a visual inspection. It can also be carried out by the apparatus 2, in particular by the control unit 10, in that the pre-stimulus distribution of $\bar{x}_j(t)$ or $|\bar{x}_j(t)|$ observed and a characteristic threshold value is determined, e.g. the 99th percentile of the pre-stimulus distribution of $|\bar{x}_j(t)|$ or simply its maximum. If now e.g. the amount of the post-stimulus response exceeds this characteristic threshold value in principle or for a predefined minimum time, e.g. 20 ms, an averaged response different from zero is present. A phase reset can be present in this case. I.e. the stimulus strength would have to be increased for so long until the post-stimulus response differs from a zero line. In addition to the method presented here that is simple, but has been proven in practice, other statistical tests known to the skilled person can be used for the signal analysis.

A more exact, but more complex, variant for investigating whether the stimuli effect a phase reset is offered by the analysis of the phase. The phase $\psi_j(t)$ of $x_j(t)$ is determined for this purpose. This is done by means of a Hilbert transformation from the signal that represents the pathological oscillatory activity and that is determined by means of band pass filtering or empirical mode decomposition. The empirical mode decomposition allows, in comparison with band pass filtering, a parameter-independent determination of physiologically relevant modes in different frequency ranges (cf. N. E. Huang et al.: The empirical mode decomposition and the Hilbert spectrum for nonlinear and non-stationary time series analysis. Proc. R. Soc. A: Math. Phys. Eng. Sci. 454:903-995 (1998)). The combination of empirical mode decomposition with a subsequent Hilbert transformation is called a Hilbert-Huang transformation (cf. N. E. Huang et al.: A confidence limit for the empirical mode decomposition and Hilbert spectral analysis, Proceedings of the Royal Society of London Series A, 459, 2317-2345 (2003)). The phase $\psi_j(t)$ can also be determined by means of wavelet analysis. A phase reset is present when the phase $\psi_j(t)$ is set to a preferred value by a stimulus (at a stimulus start at t=0) after a specific time. I.e. $\{\psi_j(\tau_k+t)\}_{k=1,\ldots,I}$ the distribution of the values of the phase $\psi_j(t)$ acquired from the I stimulus responses has a cluster point at the time t (relative to the burst start at t=0). The skilled person is aware of different methods with which it can be demonstrated that a distribution has a cluster value (that is a peak). A common method is the determination of the phase reset index $\rho(t)$ by means of a circular mean value.

$$\rho(t) = \left| \frac{1}{l} \sum_{k=1}^{l} \exp[i\psi_j(\tau_k + t)] \right| \quad (2)$$

A phase reset is present when $\rho(t)$ e.g. exceeds the maximum or the 99th percentile of the pre-stimulus distribution of $\rho(t)$ (at a point in time or within a small time window of e.g. 20 ms width).

The analysis using the averaged responses $\bar{x}_j(t)$ has proved itself sufficiently in practice.

The effects achievable using the invention described herein are illustrated with reference to simulation results in FIGS. 6 to 9. The simulation is based on a network of 200 neurons, wherein all the neurons have a highly exciting short-range coupling and a weak inhibitory long-range coupling among one another. The synaptic coupling strengths in the network can change in accordance with STPD (spike timing dependent plasticity) rules. An initially strongly coupled network produces highly synchronous neuronal activity.

Figure 6:
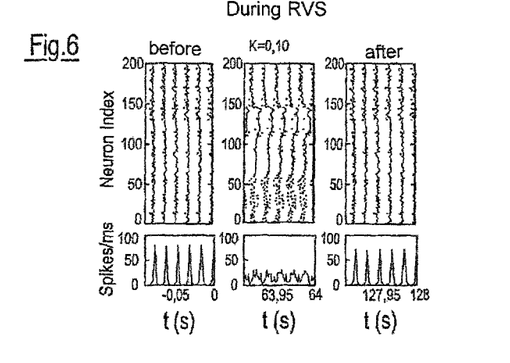
FIGS. 6 to 9 illustrate diagrams with simulation results for different CR stimulations.
Figure 7:
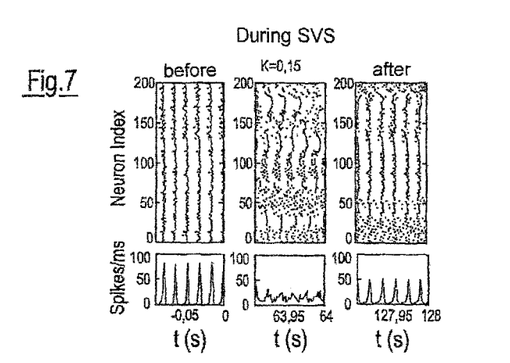

For the simulations shown in FIGS. 6 and 7, the respective CR stimulation was started at t=0 s and ended at t=64 s. The activity of the network is examined up to t=128 s, i.e. until 64 s after the end of the stimulation. Stimulation took place continuously, i.e. without cycles in which breaks were observed, during the CR stimulation.

The illustrations in the upper row in FIGS. 6 and 7 each show when each individual neuron fires during different time intervals: before, during and after application of the CR stimulation. The left hand column shows the neuronal activity during the last 80 ms before the start of the CR stimulation. The middle column shows the neuronal activity during the last 80 ms of the CR stimulation and the right hand column relates to the last 80 ms at the end of the subsequent stimulation-free time period lasting 64 s. The illustrations in the top row are raster plots of the neuronal activity, i.e. electric discharges of the individual neurons are marked as dots. The illustrations in the bottom row each show how many neurons fire simultaneously within 1 ms during the respective time periods.

A CR simulation having a fast-varying sequence and a sub-threshold stimulus level (RVS) was used for the situation shown in FIG. 6. K=0.10 was selected as the stimulus level. A CR stimulation having a slow-varying sequence and a supra-threshold stimulus level (SVS) was used for the simulation shown in FIG. 7, where the stimulus level amounted to K=0.15 and each sequence was repeated 100 times before a new sequence was applied. The network before the application of the CR stimulations in FIGS. 6 and 7 was in the same starting state.

As the middle column of FIG. 6 shows, the fast-varying CR stimulation with a low stimulus level is sufficient for an acute effect in which the degree of synchronization reduces during the CR stimulation and increases significantly again after the end of the CR stimulation. However, the sole use of a slow-varying CR stimulation at a higher stimulus level shown in FIG. 7 also does not produce any long-term desynchronization.

Figure 8:
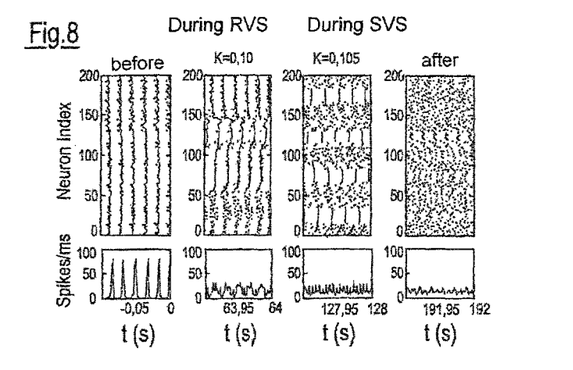

The CR stimulations from FIGS. 6 and 7 were combined with one another for the simulation shown in FIG. 8. In FIG. 8, the first column from the left shows the neuronal activity during the last 80 ms before the start of the CR stimulation. The second column shows the neuronal activity during the last 80 ms of the CR stimulation with a fast-varying sequence and a sub-threshold stimulus level. The third column shows the neuronal activity during the last 80 ms of the CR stimulation with a slow-varying sequence and a supra-threshold stimulus level. The fourth column relates to the last 80 ms at the end of the subsequent stimulation-free time period lasting 64 s. The same stimulation parameters as in FIGS. 6 and 7 were used.

It has surprisingly been found that a stimulation success that also last after 64 s after the end of the CR stimulation is obtained due to the consecutively applied CR stimulations with a fast-varying sequence and with a slow-varying sequence.

Figure 9:
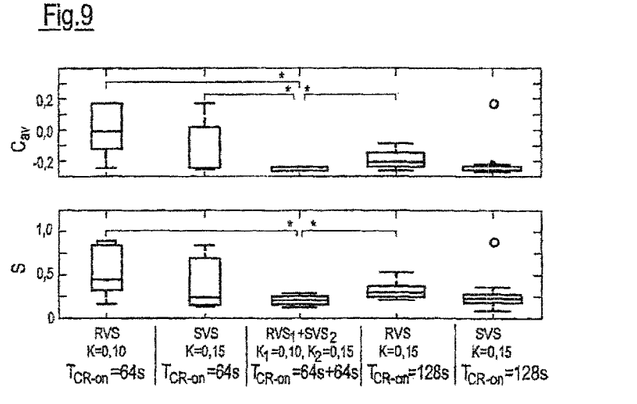

Since the starting conditions of the network and the orders of the consecutive sequences are an influence on the desynchronization, the simulations were repeated for ten other combinations of starting conditions of the network and of the sequence orders. In FIG. 9, the distributions $C_{av}$ of the resulting average values of the synaptic power and the distributions S of the synchronization after the ending of the CR stimulation with a stimulation duration of 64 s (two left hand columns) or 128 s (three right hand columns) are shown as box plots for five different combinations of CR methods and stimulus levels K. The total duration of the CR stimulation is called $T_{CR-on}$. The medians of the resulting $C_{av}$ distributions and S distributions are shown by the horizontal lines in the boxes. The box corresponds to that region in which the mean 50% of the data lie; the whiskers corresponds to the lower and upper 25% of the data respectively. Open circles designate overshoots and are defined as values that are at least 1.5 times the length of the box beneath or outside the box. A star indicates that the two-stage stimulation (middle gap) with an initial CR stimulation with a fast-varying sequence and a sub-threshold stimulus level and a subsequent CR stimulation with a slow-varying sequence and a supra-threshold stimulus level is statistically significantly more successful than the single-stage stimulation lasting 64 s to 128 s (one-sided Mann-Whitney U test, p<0.05).

The invention claimed is:
1. An apparatus for stimulating neurons, the apparatus comprising:
a stimulation unit configured to be implanted into a body of a patient and that includes a plurality of stimulation elements configured to stimulate neurons in at least one of a brain or a spinal cord of the patient with stimuli, wherein the stimuli are at least one of electrical stimuli or optical stimuli; and
a control unit configured to operates the stimulation unit during a first time interval and during a second time interval following the first time interval in different stimulation modes,
wherein the control unit controls the stimulation unit in a first stimulation mode during at least 75% of a duration of the first time interval such that the stimulation elements repetitively generate sequences of stimuli and the order in which the stimulation elements generate the stimuli within a sequence is constant for at most 5 consecutively generated sequences and then varied, wherein the control unit controls the stimulation unit in a second stimulation mode during at least 75% of a duration of the second time interval such that the stimulation elements repetitively generate sequences of stimuli and the order in which the stimulation elements generate the stimuli within a sequence is constant for at least 25 consecutively generated sequences and then varied, and wherein a level of the stimuli during the first stimulation mode is smaller than or equal to a predefined stimulus level and a level of the stimuli during the second stimulation mode is at least 1.3 times the predefined stimulus level.

2. The apparatus in accordance with claim 1, wherein the sequences of stimuli are generated in a time pattern that comprises consecutive cycles in at least one of the first or second stimulation modes, and wherein a respective sequence of stimuli is generated in at least some of the cycles.

3. The apparatus in accordance with claim 2, wherein either exactly one sequence of stimuli is generated or no stimuli are generated within a respective cycle.

4. The apparatus in accordance with claim 2, wherein stimuli are generated during n consecutive cycles and no stimuli are generated during the following m cycles, such that a pattern of the n consecutive cycles followed by m cycles is periodically continued, with n and m being nonnegative whole numbers.

5. The apparatus in accordance with claim 1, wherein a pattern according to which the order in which the stimulation elements generate the stimuli within a sequence in the first stimulation mode is constant for at most 5 consecutively generated sequences and then varied is repeated multiple times.

6. The apparatus in accordance with claim 1, wherein a pattern according to which the order in which the stimulation elements generate the stimuli within a sequence in the second stimulation mode is constant for at least 25 consecutively generated sequences and then varied is repeated multiple times.

7. The apparatus in accordance with claim 1, wherein the stimuli are configured to de synchronize a pathologically synchronous and oscillatory activity of neurons on an administration to the patient over the plurality of stimulation elements.

8. The apparatus in accordance with claim 7, wherein a duration of a cycle substantially corresponds to a mean period of the pathologically synchronous and oscillatory activity of the neurons.

9. The apparatus in accordance with claim 7, wherein the stimuli generated by the stimulation elements reset phases of neuronal activity of a plurality of subpopulations of the stimulated neurons with the pathologically synchronous and oscillatory activity at different points in time.

10. The apparatus in accordance with claim 1, wherein the stimulation unit includes L stimulation elements and P of the L stimulation elements generate stimuli in a respective sequence of stimuli, where L≥2 and 2≤P≤L.

11. The apparatus in accordance with claim 10, wherein each of the P stimulation elements generates exactly one stimulus within a respective sequence of stimuli.

12. The apparatus in accordance with claim 11, wherein exactly one stimulus is at least one of an electrical pulse train or an optical pulse train.

13. The apparatus in accordance with claim 1, further comprising a measuring unit configured to record measured signals that reproduce a neuronal activity of the neurons stimulated by the stimuli.

14. The apparatus in accordance with claim 13, wherein the control unit is configured to switch from the first stimulation mode to the second stimulation mode when the control unit determines, based on the recorded measured signals, that a degree of synchronization of the stimulated neurons is reduced by at least one predefined threshold value when the stimuli are applied in the first stimulation mode.

15. A method of stimulating neurons by a stimulation unit implanted in a body of a patient and having a plurality of stimulation elements that generates stimuli to stimulate neurons in at least one of a brain or spinal cord of the patient, the method comprising:

operating the stimulation unit in different stimulation modes during a first time interval and a second time interval following the first time interval;

operating the stimulation unit during at least 75% of a duration of the first time interval in a first stimulation mode in which the stimulation elements repetitively generate sequences of stimuli and an order in which the stimulation elements generate the stimuli within a sequence is constant for at most 5 consecutively generated sequences and then varied, wherein the stimuli are at least one of electrical stimuli or optical stimuli; and operating the stimulation unit in a second stimulation mode during at least 75% of a duration of the second time interval in which the stimulation elements repetitively generate sequences of stimuli and the order in which the stimulation elements generate the stimuli within a sequence is constant for at least 25 consecutively generated sequences and then varied, wherein a level of the stimuli in the first stimulation mode is smaller than or equal to a predefined stimulus level and a level of the stimuli in the second stimulation mode is at least 1.3 times the predefined stimulus level.

16. The method in accordance with claim 15, further comprising recording, by a measuring unit, measured signals that reproduce a neuronal activity of the neurons stimulated by the stimuli.

17. The method in accordance with claim 16, further comprising switching from the first stimulation mode to the second stimulation mode when the recorded measured signals indicate that a degree of synchronization of the stimulated neurons is reduced by at least one predefined threshold value when the stimuli are applied in the first stimulation mode.

18. A computer program product for execution in a data processing system, the computer program product including instructions for:

generating control signals to control a stimulation unit implanted in a body of a patient, wherein the stimulation unit includes a plurality of stimulation elements configured to generate stimuli for stimulating neurons in at least one of a brain or a spinal cord of the patient, wherein the stimuli are at least one of electrical stimuli or optical stimuli:

operating the stimulation unit in different stimulation modes during a first time interval and a second time interval following the first time interval;

operating the stimulation unit during at least 75% of a duration of the first time interval in a first stimulation mode in which the stimulation elements repetitively generate sequences of stimuli and an order in which the stimulation elements generate the stimuli within a sequence is constant for at most 5 consecutively generated sequences and then varied; and operating the stimulation unit during at least 75% of a duration of the second time interval in a second stimulation mode in which the stimulation elements repetitively generate sequences of stimuli and an order in which the stimulation elements generate the stimuli within a sequence is constant for at least 25 consecutively generated sequences and then varied, wherein a level of the stimuli in the first stimulation mode is smaller than or equal to a predefined stimulus level and a level of the stimuli in the second stimulation mode is at least 1.3 times the predefined stimulus level.

19. The computer program product in accordance with claim 18, wherein the instructions further comprise recording, by a measuring unit, measured signals that reproduce a neuronal activity of the neurons stimulated by the stimuli.

20. The computer program product in accordance with claim 19, wherein the instructions further comprise switching from the first stimulation mode to the second stimulation mode when the recorded measured signals indicate that a degree of synchronization of the stimulated neurons is reduced by at least one predefined threshold value when the stimuli are applied in the first stimulation mode.

* * * * *